(12) United States Patent
Gabl et al.

(10) Patent No.: US 8,240,907 B2
(45) Date of Patent: Aug. 14, 2012

(54) APPARATUS AND METHOD FOR MOVING A LIQUID BY MEANS OF A PIEZOELECTRIC TRANSDUCER

(75) Inventors: Reinhard Gabl, St. Peter im Sulmtal (AT); Mathias Link, München (DE); Matthias Schreiter, München (DE); Jan Weber, München (DE)

(73) Assignee: Siemens Aktiengesellschaft, Munich (DE)

( * ) Notice: Subject to any disclaimer, the term of this patent is extended or adjusted under 35 U.S.C. 154(b) by 1031 days.

(21) Appl. No.: 12/066,085

(22) PCT Filed: Sep. 7, 2006

(86) PCT No.: PCT/EP2006/066139
§ 371 (c)(1),
(2), (4) Date: Mar. 7, 2008

(87) PCT Pub. No.: WO2007/028820
PCT Pub. Date: Mar. 15, 2007

(65) Prior Publication Data
US 2008/0247264 A1    Oct. 9, 2008

(30) Foreign Application Priority Data

Sep. 9, 2005   (DE) .......................... 10 2005 043 034

(51) Int. Cl.
*B01F 11/02*   (2006.01)
(52) U.S. Cl. .................................... 366/127; 366/DIG. 4
(58) Field of Classification Search ............. 310/323.21, 310/324; 366/127, DIG. 4
See application file for complete search history.

(56) References Cited

U.S. PATENT DOCUMENTS

| | | | | |
|---|---|---|---|---|
| 2,702,691 A | * | 2/1955 | Virmani | 366/127 |
| 4,502,932 A | * | 3/1985 | Kline et al. | 204/192.18 |
| 4,527,901 A | * | 7/1985 | Cook | 366/127 |
| 4,719,383 A | * | 1/1988 | Wang et al. | 310/324 |
| 4,751,419 A | * | 6/1988 | Takahata | 310/324 |

(Continued)

FOREIGN PATENT DOCUMENTS

DE        100 62 246 C1    5/2002

(Continued)

OTHER PUBLICATIONS

Kim, "Microfluidic motion generation with acoustic waves," Sensors and Actuators A, vol. 66, No. 1-3, pp. 355-360 (Apr. 1, 1998).

(Continued)

*Primary Examiner* — Charles E Cooley
(74) *Attorney, Agent, or Firm* — Young & Thompson (57) ABSTRACT

An apparatus having a device for moving a liquid comprises a piezoacoustic resonator element (11) having at least one piezoelectric layer (110) and two electrodes (111 and 112) present on the piezoelectric layer (110). The piezoacoustic resonator element (11) is designed such that, owing to a voltage being applied to the piezoelectric layer (110) by means of the electrodes (111 or 112), a volume oscillation of the piezoelectric layer (110) is excited at a resonant frequency. The piezoelectric resonator element (11) can be acoustically coupled in a suitable manner to a liquid for the purpose of transmitting the excited oscillation into the liquid for the purpose of moving the liquid. The apparatus may be in the form of a micromixer or in the form of a micropump and may comprise, in addition, sensor elements (41) for detecting the attachment of substance.

20 Claims, 5 Drawing Sheets

U.S. PATENT DOCUMENTS

| | | | | |
|---|---|---|---|---|
| 4,761,582 A | * | 8/1988 | McKee | 310/322 |
| 4,868,447 A | * | 9/1989 | Lee et al. | 310/328 |
| 4,870,313 A | * | 9/1989 | Hirama et al. | 310/320 |
| 5,006,749 A | | 4/1991 | White | |
| 5,674,742 A | * | 10/1997 | Northrup et al. | 435/286.5 |
| 5,801,476 A | * | 9/1998 | Sturzebecher et al. | 310/324 |
| 5,932,953 A | * | 8/1999 | Drees et al. | 310/324 |
| 6,010,316 A | | 1/2000 | Haller et al. | |
| 6,326,563 B1 | * | 12/2001 | Takeuchi et al. | 177/210 FP |
| 6,361,747 B1 | * | 3/2002 | Dion et al. | 422/128 |
| 6,396,200 B2 | * | 5/2002 | Misu et al. | 310/348 |
| 6,458,325 B1 | | 10/2002 | Roscher et al. | |
| 6,568,052 B1 | * | 5/2003 | Rife et al. | 29/25.35 |
| 6,586,861 B2 | * | 7/2003 | Misu et al. | 310/324 |
| 6,719,449 B1 | | 4/2004 | Laugharn et al. | 366/127 |
| 6,941,624 B2 | | 9/2005 | Asano | 29/25.35 |
| 7,317,276 B2 | | 1/2008 | Sugahara | 310/365 |
| 7,468,608 B2 | * | 12/2008 | Feucht et al. | 324/633 |
| 8,038,337 B2 | * | 10/2011 | Rathgeber et al. | 366/115 |
| 8,079,748 B2 | * | 12/2011 | Murakami | 366/116 |
| 2003/0076007 A1 | * | 4/2003 | Murai | 310/324 |
| 2003/0127946 A1 | * | 7/2003 | Yamada et al. | 310/324 |
| 2004/0066703 A1 | * | 4/2004 | Sparey-Taylor et al. | 366/127 |
| 2004/0072366 A1 | | 4/2004 | Wixforth et al. | |
| 2004/0256961 A1 | * | 12/2004 | Namba et al. | 310/365 |
| 2006/0078473 A1 | | 4/2006 | Murakami | |
| 2006/0125489 A1 | * | 6/2006 | Feucht et al. | 324/633 |
| 2008/0316477 A1 | * | 12/2008 | Murakami | 356/244 |
| 2009/0079442 A1 | * | 3/2009 | Gabl et al. | 324/663 |
| 2010/0008178 A1 | * | 1/2010 | Fahrion | 366/110 |

FOREIGN PATENT DOCUMENTS

| | | |
|---|---|---|
| DE | 103 39 996 A1 | 4/2005 |
| EP | 0 844 478 A1 | 5/1998 |
| EP | 1 161 294 B1 | 7/2002 |
| WO | 03/079006 A1 | 9/2003 |
| WO | 2004/017063 A2 | 2/2004 |
| WO | 2004/102203 A1 | 11/2004 |

OTHER PUBLICATIONS

Vivek et al., "Novel Acoustic-Wave Micromixer," Proc. IEEE Micro Electro Mech Syst Mems, Proc of the IEEE Micro Electro Mech Syst (MEMS), pp. 668-673 (Jan. 23, 2000).

* cited by examiner

APPARATUS AND METHOD FOR MOVING A LIQUID BY MEANS OF A PIEZOELECTRIC TRANSDUCER

The invention relates to an apparatus having a device for moving a liquid and to a method for moving a liquid using such an apparatus.

Due to their size and the relatively small liquid volumes available, microfluidic systems, which are used as biosensors for example, require a system of microchannels with small cross sections. Because of these small cross sections and the relatively small liquid speeds, the Reynolds numbers of systems of this kind, which characterize the ratio of inertial to viscous forces and which are infinitely large for an ideal non-viscous liquid, are very small. It follows from this that the flows in these channels are predominantly laminar and consequently adequate mixing does not take place.

Such mixing is necessary with biosensors, for example, to accelerate the polymerase chain reaction (PCR) and also to effect the hybridization of DNA, as in both cases these are diffusion-limited processes.

To solve this problem, a surface wave resonator based on a lithium niobate chip has recently been proposed, which works with an HF power up to 500 mW at 140 MHz. This produces a quasi-chaotic mixing of the liquid, as a result of which, for example, the hybridization can be completed in a few minutes.

However, solutions of this kind are often limited with regard to size and frequency range.

The object of the invention is to specify an improved apparatus having a device for moving a liquid, and a method for moving a liquid using an apparatus of this kind.

According to the invention, the apparatus comprises a device for moving a liquid having at least one piezoacoustic resonator element and two electrodes, which abut the piezoelectric layer, the piezoacoustic resonator element being made in such a way that by applying a voltage to the piezoelectric layer by means of the electrodes a volume oscillation of the piezoelectric layer, which is transmitted to the liquid, is excited at resonant frequency.

Piezoacoustic resonator elements of this kind are known from technology as so-called BAW (bulk acoustic wave) resonators and have been developed as passive components for high-frequency applications, for example in mobile radio technology.

In the case of BAW resonators, in contrast to surface wave resonators (SAW—Surface Acoustic Wave Resonator), an acoustic volume oscillation (structure-borne sound oscillation) of the piezoelectric layer is excited and not a surface wave. Depending on the configuration of the piezoacoustic resonator, the excited volume oscillation of the piezoacoustic resonator element can be a longitudinal oscillation and/or a volume shear oscillation. As an example, in the case of vertical crystallographic orientation of the c-axis of a hexagonal piezoelectric material, e.g. PZT (lead zirconate titanate), a longitudinal oscillation can be produced along the layer thickness of the piezoelectric layer when electrodes are arranged on the top and bottom (sandwich structure). On the other hand, a volume shear oscillation is produced along the lateral extension of the piezoelectric layer by orientating the polycrystalline layer in such a way that the c-axis runs in the plane of the layer.

Preferably, the piezoacoustic resonator element of the apparatus according to the invention works in such a way that a longitudinal oscillation is excited. Preferably, the piezoacoustic resonator element works in the frequency range of 0.5 to 10 GHz, a strongly damped wave being generated in the liquid, which leads to the mixing of the liquid.

Preferably, the device comprises several piezoacoustic resonator elements, which are activated in anti-phase. Larger liquid volumes can also be mixed by this means, as a turbulence in the liquid and a better mixing are produced as a result of the anti-phase activation.

The size of the piezoacoustic resonator element of the device according to the invention is preferably 50 to 200 µm. A significant advantage compared with existing solutions is the increased potential for miniaturization, as a result of which the size of the overall microfluidic system can be considerably restricted.

The device for moving a liquid according to the present invention can be designed in the form of a mixing device and/or a pumping device. In the form of a micropump, it can be arranged on a membrane, for example, which undergoes a bending deflection as a result of activating the piezoacoustic resonator element. Preferably, the thickness of a piezoacoustic resonator element is a half wavelength ($\lambda/2$).

The apparatus can be designed in the form of a module. The module can be designed in such a way that it can be integrated into a microfluidic system, e.g. simply by inserting or plugging in.

In a simple embodiment of the piezoacoustic resonator element, said element is arranged on an acoustic mirror, which comprises several layers with strongly differing acoustic impedance. The piezoacoustic resonator element can however also be arranged on a thin-film membrane, which can be made by rear-etching a silicon wafer for example with a nitridic or oxidic covering layer for example as an etch stop. In doing so, the apparatus can be designed as a micropump, wherein, as a result of activating the piezoacoustic resonator element, the membrane undergoes a bending deflection, the oscillation of which is transmitted into the liquid.

An improved pump performance can be achieved when the apparatus comprises several piezoacoustic resonator elements, which are activated in anti-phase. In a particularly advantageous embodiment, the apparatus is designed in the form of a multi-membrane counter-contact pump, wherein several piezoacoustic resonator elements are provided in a flow channel one behind the other in the direction of flow as actuators (pumps), and a return flow barrier is arranged between two of the piezoacoustic resonator elements.

Particular advantages are provided by the ability to integrate the apparatus according to the invention, which has a device for moving a liquid, which can be integrated in a simple manner on a semiconductor substrate in the form of a thin-film component. In doing so, the usual method processes of semiconductor technology can be used, such as bipolar, CMOS or BiCMOS technology for example.

The apparatus can be fixed on a high-frequency substrate by flip-chip assembly. The HF substrate can be part of a module, which can be easily integrated into the housing of a flow cell. The high-frequency substrate is preferably an LTCC (Low Temperature Cofired Ceramic) substrate.

With regard to the miniaturization capability, a particular advantage of the apparatus according to the invention lies in the fact that it can be integrated with a sensor for detecting a substance in the simplest manner using the same technology platform. Such a device for detecting a substance can be a sensor, which detects certain substances from a mixture, but can also be a mass sensor for example.

By detecting the adsorption of a certain substance, the sensor function can include the selective determination of this substance from a substance mixture, the determination of the concentration of the appropriate substance, the determination of the mass, the reaction kinetics etc.

Sensors of this kind based on a piezoacoustic volume resonator are known from the technology. For example, the applicant's application WO 2004/017063 A2 describes a microsensor of this kind for measuring the adsorption of a substance by the surface of the BAW resonator. As a result of the adsorption of the substance, the resonant frequency of the BAW resonator changes so that a conclusion can be drawn relating to the adsorption of the substance. A device of this kind for detecting a substance has a surface section, which is arranged for adsorbing the substance to be detected and can be made differently for different substances to be detected.

By combining or integrating the functions of the apparatus according to the invention for moving a liquid having a device for detecting a substance, new areas of application can be opened up. For example, the monitoring of micro reactions is made possible in that reaction products can be detected at the same time. As sensor elements and actuator elements are realized in the form of integrated semiconductor components on the same chip, the apparatus can be implemented in the smallest space, as a result of which considerably less volumes of the reagents are required, which in many cases is accompanied by a considerable cost saving. Furthermore, the possibility is opened up of manufacturing arrays with several elements, which enable different tests to be carried out in parallel.

At the same time, the apparatus can comprise a plurality of piezoacoustic resonators with different oscillation modes on excitation. For example, it is possible to provide a first piezoacoustic resonator element with thickness resonance mode and a further resonator element with shear oscillation mode. In doing so, the apparatus can be designed in such a way that the two piezoacoustic resonator elements are activated by different drive devices, i.e. operated individually.

In a particularly preferred embodiment, the two piezoacoustic resonator elements are arranged one above the other in the form of a stack. In doing so, the top resonator element can be designed as a sensor element and preferably have a thickness, which is equal to λ/2. In this case, the top element can act like an anti-reflection coating for the acoustic wave, which enables energy to be transmitted into the liquid particularly efficiently when mixing.

A particularly efficient and strongly miniaturized apparatus according to the invention is an MEMS (Microelectronic Mechanical System) with integral biosensor. This comprises a first piezoacoustic resonator element, which causes a bending deflection of a membrane when it is activated. In addition, a second piezoacoustic resonator element is provided, which is operated in anti-phase. The two piezoacoustic resonator elements are arranged one behind the other within a flow channel of a flow cell. A return flow barrier is located between them in the flow cell. A device for detecting a substance, which has an appropriate coating for adsorbing a substance to be detected, is in each case provided on the top of the two piezoacoustic resonator elements, which act as a pump.

The combinations sensor and mixing element or sensor and pump element as examples of a microsystem technology component, which serves several functions, can be realized in this way by the apparatus according to the invention. The considerably reduced size opens up new areas of application and reduces the manufacturing costs.

Because of the silicon-compatibility of the piezoacoustic resonator elements, a design in the form of a lab-on-a-chip system is also possible, as it combines appropriate mixing and sensor functions with appropriate integral evaluation devices.

The invention is not restricted to embodiments of this kind, however, and also provides a device with at least one piezoacoustic resonator element, which is designed in such a way that, by activating the electrodes of this one piezoacoustic resonator element, a longitudinal volume oscillation and, at the same time, a shear mode volume oscillation of the piezoelectric layer can be excited.

A piezoacoustic resonator element of this kind can be produced by specific selection of the crystallographic orientation of the piezoelectric layer. For example, the piezoelectric layer can be one consisting of ZnO, the crystallographic c-axis of which is tilted in a suitable manner. The tilt can be 16° for example. As well as ZnO, AlN or PZT (lead zirconate titanate) with suitable tilt can be used. In a configuration of this kind, the liquid is moved and measured at the same time with one piezoacoustic resonator element. Accordingly, sensor and actuator function are provided with one piezoacoustic resonator element.

In this embodiment having a piezoacoustic resonator element, which acts as sensor and actuator simultaneously, both longitudinal modes and shear modes can be excited with comparable strength. Liquids can be mixed in longitudinal modes, as this mode couples very well in the liquid. Gravimetric measurements, for example, can be carried out in shear modes as an example of detecting a substance.

Considerable advantages also arise with an embodiment of this kind with regard to the manufacturing processes, as only one piezoacoustic resonator element has to be processed. As this can be carried out using standard semiconductor processes, an integration with further functional units, such as an oscillator, evaluation circuit, etc, is possible without any problems. No moving parts or membranes or cantilevers are required, which brings with it simple manufacturing processes and also a higher reliability of the resulting apparatus.

Miniaturization is further promoted by combining the two functions actuator/sensor in one component, and microfluidic components can be provided, the external dimensions of which are considerably less than 100 μm, preferably less than 50 μm.

The invention also provides a method for moving a liquid using an apparatus according to the invention. The method includes the following steps: Bringing the device for moving a liquid of the apparatus according to the invention into contact with the liquid, and exciting a volume oscillation of the piezoelectric layer to resonance.

Exemplary embodiments and details of the present invention are described below with reference to the figures.

Two basic structures of a device according to the invention for moving a liquid are presented below with reference to FIGS. 1 and 2.

Figure 1:
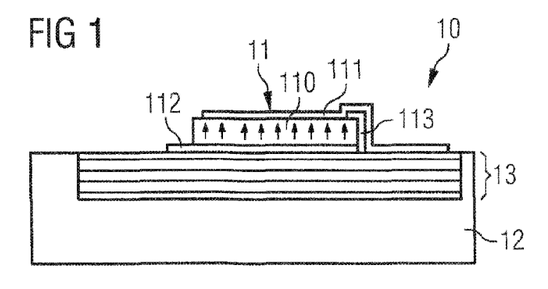
FIG. 1 shows a first exemplary embodiment of a device for moving a liquid having a piezoacoustic resonator element schematically in cross section.

FIG. 1 shows a first exemplary embodiment of an apparatus having a device for moving a liquid in which the piezoacoustic resonator element is arranged on a carrier substrate.

The apparatus 10 comprises a piezoacoustic resonator element 11, which is arranged on a silicon wafer as substrate 12. The piezoacoustic resonator element 11 comprises a piezoelectric layer 110 made from PZT with a layer thickness of 1 μm. Electrodes 111 and 112 made from platinum with a layer thickness of 500 nm are attached to the top and bottom respectively of the piezoelectric layer 110. An insulation 113 made from $Al_2O_3$ is provided between the electrodes 111, 112. The bottom electrode 112 is arranged on an acoustic mirror 13 consisting of several alternate layers with strongly differing acoustic impedance. These can be layers of $W/SiO_2$ for example. This acoustic mirror, which functions as a Bragg reflector, serves to prevent acoustic losses in the substrate 12. The layer thickness of the individual layers of the mirror is $\lambda/4$.

Instead of being arranged on a piezoacoustic mirror, the piezoacoustic resonator element can also be arranged on a thin membrane. An embodiment of this kind is shown in FIG. 2. The same references as in FIG. 1 designate the same parts. The membrane 24, on which the piezoacoustic resonator element 11 is arranged, is made of $SiO_2$. The membrane 24 forms a covering layer on the silicon wafer 23.

The processing of the wafer for producing the membrane is carried out by rear etching, as a consequence of which the rear recess 25 of the silicon wafer 23 is formed by the removal of material. In doing so, the $SiO_2$ layer 24 acts as an etch stop and forms the membrane in the finished component.

Figure 2:
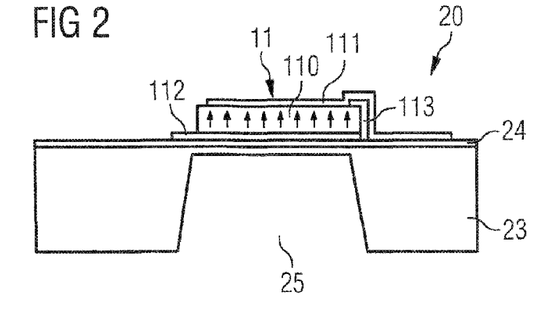
FIG. 2 shows a second exemplary embodiment of a device for moving a liquid having a piezoacoustic resonator element schematically in cross section.

In both exemplary embodiments, which are shown in FIGS. 1 and 2, the piezoacoustic thin-film resonator 11 works in the thickness resonance mode. At the same time, the crystallographic orientation of the piezoelectric layer is a <111> orientation. This has the advantage that the resulting oscillation can be transmitted into the liquid particularly well so that an efficient pumping or mixing is possible.

Figure 3:
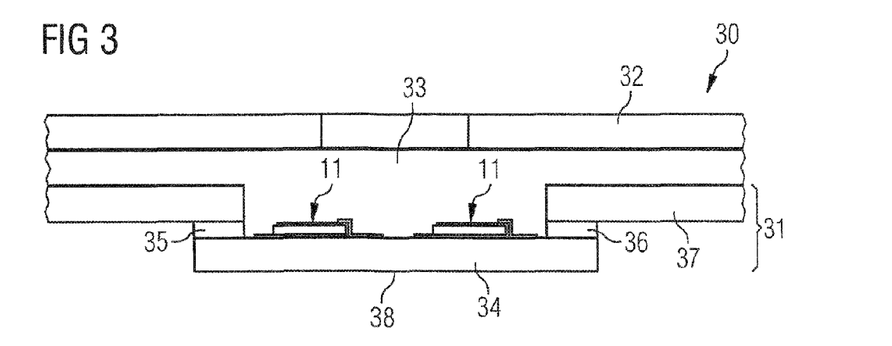
FIG. 3 shows an exemplary embodiment of an apparatus according to the invention, which is designed as a micromixer, schematically in cross section.

A schematic detail of a cross section of an embodiment is shown in FIG. 3 in which the apparatus according to the invention is designed in the form of a complete microfluidic system.

The microfluidic system 13 comprises a housing, of which a housing section 32 is shown in FIG. 3, which borders a flow channel 33. A liquid, which is to be analyzed in a section (not shown) of the apparatus 30, flows through this flow channel 33. For this purpose, the microfluidic system comprises a module 31 for mixing the liquid flowing through the flow channel 33. This module 31 comprises a mixer chip 38, on which two piezoacoustic resonator elements 11 are arranged behind one another in the direction of flow, the structure of which is the same as the piezoacoustic resonator elements 11 described in FIGS. 1 and 2, with the exception that here the external dimensions of the piezoacoustic resonator elements are 250×100×50 μm with a film thickness of the piezoelectric layer of 30 μm. The mixer chip 38 is an LTCC (Low Temperature Cofire Ceramic) substrate 37 bonded by means of flip-chip technology. The LTCC substrate can contain further passive electronic components in the usual way. At the same time, a top part section of the mixer chip 38 is connected by means of so-called solder bonds 35 to the high-frequency substrate 37. The solder bonds 35 are made from a gold-nickel alloy. An underfill 36 is also provided. In an underfill process for producing the underfill 36, a bead of material is applied along the edge of the chip, wherein the liquid flows under the chip due to the capillary effect.

The structure shown in FIG. 3, in which the mixer chip 38 is bonded directly to a high-frequency substrate 37 using flip-chip technology, provides many advantages: It results in a module 31, which can be integrated directly into the microfluidic system so that a considerable miniaturization and integration can be achieved. With regard to high-frequency technology, connection to the HF substrate by means of solder bonds also has the advantage that the high internal losses caused by bonding wires at frequencies in the gigahertz range can be avoided.

Figure 4:
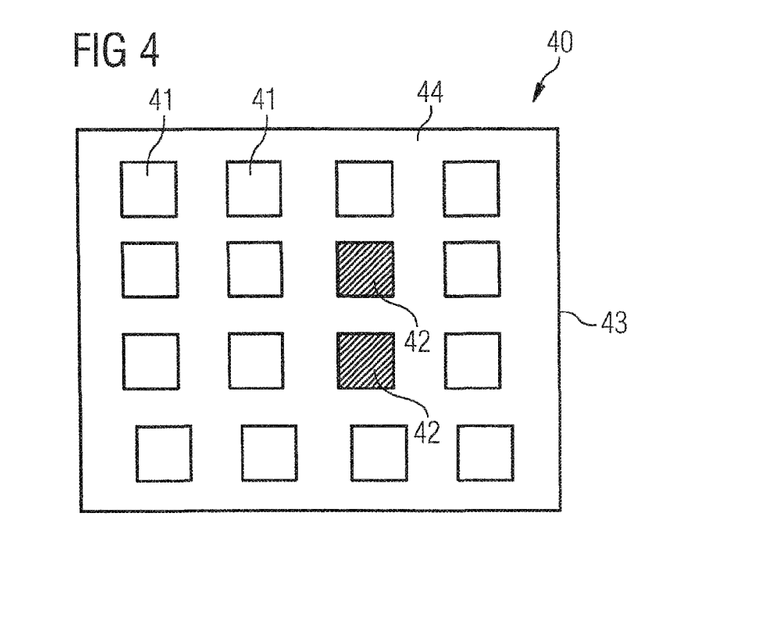
FIG. 4 shows a further exemplary embodiment of an apparatus according to the invention, which consists of sensor elements and actuator elements and which is designed in the form of an array, schematically in plan view.

An exemplary embodiment of the apparatus according to the invention, in which the 4×4 piezoacoustic resonator elements 41, 42 are arranged on a carrier substrate 44 to form an array 40, is shown in FIG. 4. Here, the piezoacoustic resonator elements 41 are designed as sensor elements for detecting a substance for the purpose of identifying or determining its concentration by measuring the adsorbed mass. A fundamental difference between the piezoacoustic resonator elements 41 and 42 consists in the different orientation of the piezoelectric thin film. In the case of the piezoacoustic resonator elements 42 this is chosen so that a longitudinal volume oscillation results while the oscillations in the case of the sensor elements 41 are shear oscillations. Due to the different orientation of the piezoelectric layers, in the case of the array 40, a further structuring plane is required for combining sensor elements 41 and actuator elements 42. The arrangement of several sensor elements 41 to form an array has the advantage of increased local resolution in the measurement.

Figure 5:
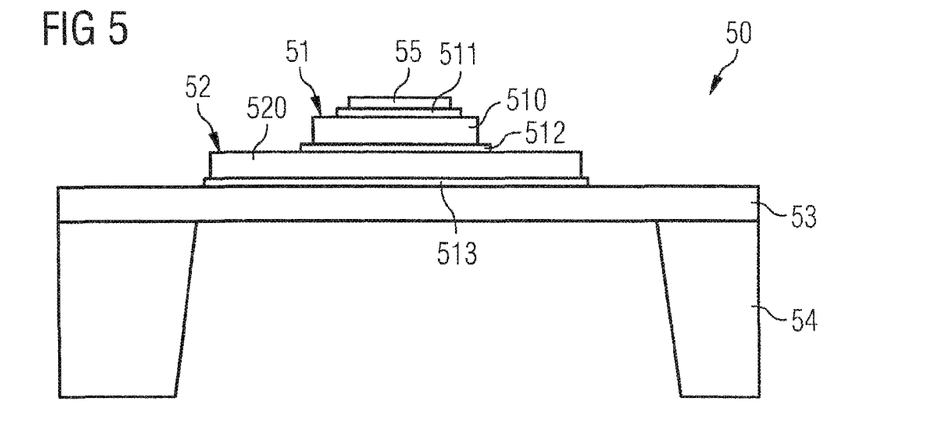
FIG. 5 shows a further exemplary embodiment of an apparatus according to the invention having several piezoacoustic resonator elements in a stack arrangement schematically in cross section.

A stack type of construction is also possible when combining sensor elements and actuator elements. A corresponding exemplary embodiment is shown in FIG. 5. In this exemplary embodiment, the apparatus according to the invention is designed as a thin-film mixer with integral biosensor. The apparatus 50 comprises a first piezoacoustic resonator element 51, which is designed as a sensor element. It is made from a piezoelectric layer 510 of ZnO with a layer thickness of 1.5 μm. Electrodes 511 and 512 with a layer thickness of 0.5 μm, which are made from an Ag/Pd alloy, are attached to the top and bottom respectively of the piezoelectric layer 510. A sensitive coating 55 is applied to the top of the top electrode 511. In the present exemplary embodiment, this is a special DNA coating, which enables a docking of a corresponding DNA for selective adsorption from a mixture of different substances using the key-lock principle. The piezoelectric layer 510 has a shear orientation corresponding to the sensor function of the piezoacoustic resonator element 51.

In this exemplary embodiment, the sensor element 51 is arranged in the form of a stack on an actuator element 52. The corresponding piezoacoustic resonator element 52 consists of a top electrode 512 and a bottom electrode 513, which are made from Ag/Pd. The piezoelectric layer 520 is made from AlN with a layer thickness of 500 nm. The length of the piezoacoustic resonator element 52 is 100 μm with a width of 50 μm. The piezoacoustic resonator element 52, which functions as an actuator, is arranged on a membrane 53 of a silicon wafer 54, which is made of silicon nitride.

A further miniaturization can be achieved as a result of the stack arrangement.

A carrier substrate with acoustic mirror can also be provided instead of the structure on the membrane 53. This must be sized so that the reflection is adequate for the frequency range of both the volume and the shear oscillation.

In the exemplary embodiment shown in FIG. 5, the thickness of the top resonator element 51 is $\lambda/2$. As a result of this, the top element acts like an anti-reflection coating for the acoustic wave, which enables energy to be transmitted into the liquid particularly efficiently when mixing.

Figure 6:
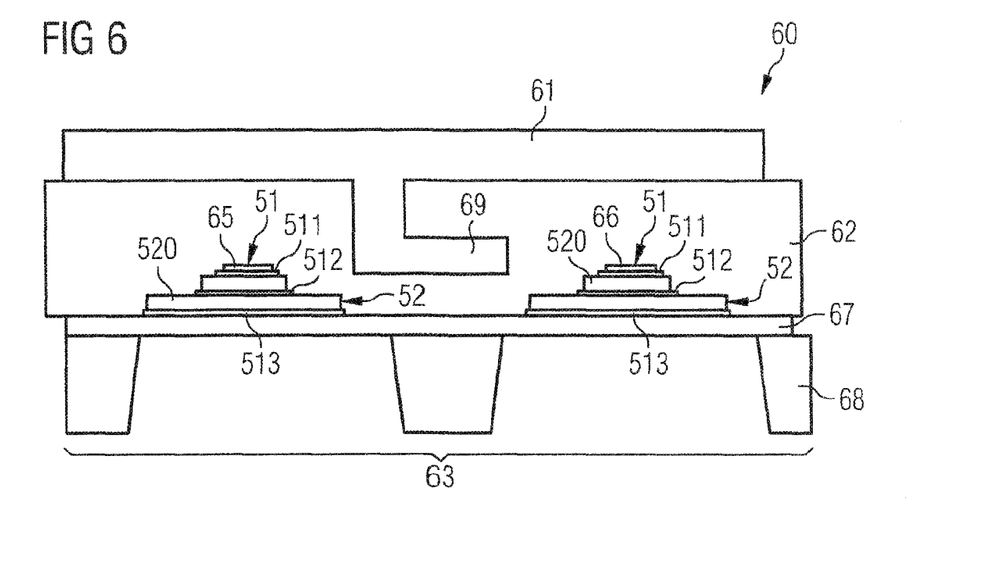
FIG. 6 shows an exemplary embodiment of an apparatus according to the invention, which is designed as an MEMS pump having integral sensor elements, schematically in cross section.

FIG. 6 shows an exemplary embodiment in which the apparatus according to the invention is designed as an MEMS (Microelectronic Mechanical System) pump with integral biosensors.

The apparatus 60, of which a detail is shown in cross section in FIG. 6, comprises a flow cell 61, which borders the top of a channel 62. The bottom of the channel 62 is formed by a counter-contact pump 63 with integral sensor elements, which is designed as a dual-membrane counter-contact pump. The micropump 63 comprises two piezoacoustic resonator elements 52 with a piezoelectric layer 520 in thickness orientation, which are arranged behind one another along the flow channel 62 and are activated in anti-phase. The structure of the piezoacoustic resonator elements 52 corresponds to that of the piezoacoustic resonator elements 52 shown in FIG. 5. A bending deflection of the membrane is produced by activating the electrodes 512 and 513 respectively. The two piezoacoustic resonator elements 52 with actuator function are activated in anti-phase. A return flow barrier 69, which is formed in one piece with the housing section 61 of the flow cell, is arranged in the flow channel. This prevents the return flow of the liquid. Because of the bimorphous structure, a membrane bending deflection with resonant frequency in the kHz range is used. In a similar way to that shown in FIG. 5, a piezoacoustic resonator element 51, which works as a sensor, is likewise arranged on the top of the piezoacoustic resonator element 52. The piezoacoustic resonator element 51 arranged upstream has a coating 66, which is made of a polymer and is suitable for absorbing certain hydrocarbons. The piezoacoustic resonator element 51 arranged downstream has a coating 65, which is made from a different polymer, which selectively adsorbs certain biomolecules. In contrast to the piezoacoustic resonator elements 52, which work as pump elements in the kHz range, the piezoacoustic resonator elements 51 work in the gigahertz range.

As a result of the arrangement of the piezoacoustic resonator elements with different function in a stack type of construction, a considerable miniaturization, which allows microsystem technology components with different functions to be realized in one component, is also possible with this exemplary embodiment.

Figure 7:
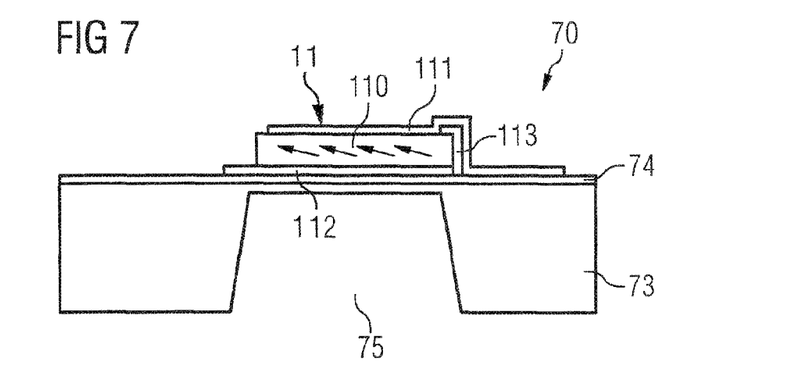
FIG. 7 shows a further exemplary embodiment of a device according to the invention for moving a liquid schematically in cross section.
Figure 8:
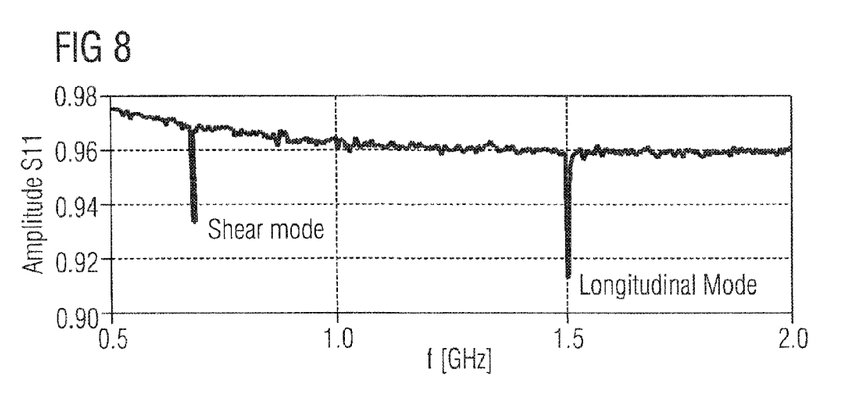
FIG. 8 shows the amplitude S11 as a function of the frequency, measured on the piezoacoustic resonator element of FIG. 8.
Figure 9:
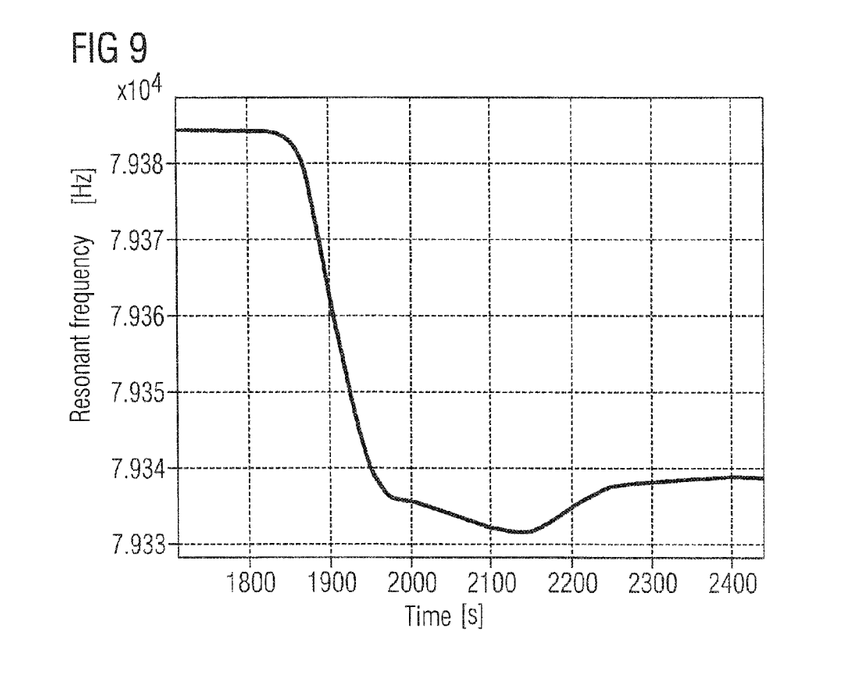
FIG. 9 shows the measurement of the resonant frequency as a function of time for the adsorption of avidin measured in shear mode at 790 MHz.

However, the invention is not restricted to exemplary embodiments in which several piezoacoustic resonators are required in order to realize the actuator function and the sensor function in one component. The invention likewise includes an apparatus having a device, which comprises a piezoacoustic resonator element, the piezoelectric layer of which is orientated in such a way that, by activating the electrodes, a volume oscillation can be excited with longitudinal mode and a volume oscillation can be excited with shear mode. An apparatus with a device made in this way for moving a liquid is shown in FIG. 7. The structure of the apparatus 70 shown in FIG. 7 corresponds to the structure of FIG. 2 with the difference that a piezoelectric layer made from ZnO with a crystallographic orientation of the c-axis virtually in the layer plane of the piezoelectric layer is used in the exemplary embodiment of FIG. 7. In this exemplary embodiment, the tilt is 16°. In the case of an orientation of this kind, longitudinal modes as well as shear modes with comparable strength can be excited as shown in FIG. 8. Liquids can be mixed on the resonator with the help of longitudinal modes, as in this case there is a good coupling into the liquid. Sensor functions can be realized by means of shear modes. By way of example, FIG. 9 shows the example of a gravimetric measurement of the adsorption of avidin measured in shear mode at 790 MHz.

This exemplary embodiment has the advantage that longitudinal modes and shear modes can be excited at the same time with only one piezoacoustic resonator element, as a result of which it becomes possible to combine actuator and sensor function in only one piezoacoustic resonator element. In the exemplary embodiment of FIG. 7, the piezoacoustic resonator element is operated by means of a signal mixer, which is not shown in the figure. This signal mixer superimposes appropriate frequencies, which are suitable for exciting the respective modes.

In FIG. 7, the piezoacoustic resonator element 701 is formed on a membrane. However, by way of example, the structure on a carrier substrate with acoustic mirror shown in FIG. 1 can also be used.

As well as the exemplary embodiment shown in FIG. 7, in which the piezoelectric layer is made from ZnO, other piezoelectric materials such as AlN and PZT with appropriate suitable tilt can be used. In the case of piezoelectric materials with hexagonal crystal structure, in many cases a preferred orientation lies in the range <45°.

Different modifications of the exemplary embodiments described above are possible, wherein individual characteristics of the different embodiments can be combined with one another or can replace one another. Where modifications of this kind are clearly apparent to the person skilled in the art, they are intended to be implicitly disclosed by the description of the exemplary embodiments explained. For example, it is not only possible to combine actuator and sensor functions in an array, but also to vary the structure of the piezoacoustic resonator element in such a way that individual piezoacoustic resonator elements are suitable for simultaneously exciting longitudinal and shear modes, and in addition piezoacoustic resonator elements are provided, which realize the corresponding function as a separate component.

Figure 10:
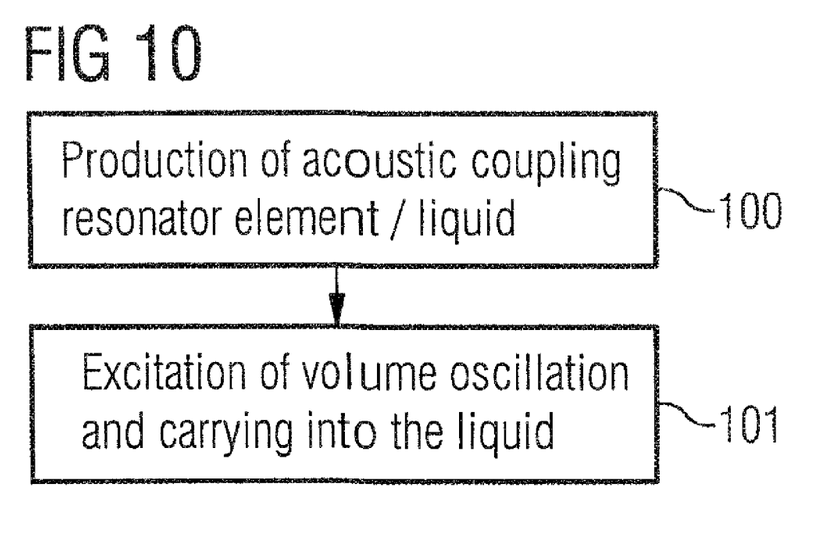
FIG. 10 shows a method sequence of an exemplary embodiment of a method for moving a liquid.

An exemplary embodiment of a method for moving a liquid using an apparatus according to the invention is described below with reference to FIG. 10.

In step 100, a liquid is brought into contact with an apparatus according to the invention in such a way that a volume oscillation of the piezoacoustic resonator element of the apparatus according to the invention can be carried into the liquid. In step 101, the movement of the liquid occurs by exciting a volume oscillation of the piezoacoustic resonator element, which is transmitted into the liquid in order to move it.

The invention claimed is:

1. An apparatus for disturbing a liquid, the apparatus comprising:
   a channel having an inlet adapted to receive a liquid and an outlet adapted to discharge the liquid separate from the inlet;
   at least one piezoacoustic resonator element (11) having at least one piezoelectric layer (110) and two electrodes (111, 112), which abut the piezoelectric layer (110), the piezoacoustic resonator element (11) being affixed to a first interior wall of the channel between the inlet and the outlet so that the at least one piezoelectric layer is exposed to the liquid in the channel and so that by applying a voltage to the piezoelectric layer (110) by means of the electrodes (111, 112) a volume oscillation of the piezoelectric layer (110) is excited at resonant frequency and disturbs the liquid in the channel.

2. The apparatus as claimed in claim 1, wherein the excited volume oscillation of the piezoacoustic resonator element (11) is a longitudinal oscillation.

3. The apparatus as claimed in claim 1, wherein the resonant frequency is in the frequency range of 0.5-4 GHz.

4. The apparatus as claimed in claim 1, comprising a plurality of the piezoacoustic resonator element (11).

5. The apparatus as claimed in claim 4, wherein the plurality of piezoacoustic resonator elements (11) are arranged to be activated in anti-phase.

6. The apparatus as claimed in claim 1, wherein a thickness of the piezoacoustic resonator element (11) is $\lambda/2$.

7. The apparatus as claimed in claim 1, wherein the at least one piezoacoustic resonator element (11) is arranged on a membrane (24).

8. The apparatus as claimed in claim 7, wherein the membrane (24) is arranged to undergo a bending deflection as a result of activating the piezoacoustic resonator element (11).

9. The apparatus as claimed in claim 7, wherein the apparatus is a multi-membrane counter-contact pump having at least two piezoacoustic resonator elements (11) arranged to be activated in anti-phase.

10. The apparatus as claimed in claim 7, comprising at least two of the piezoacoustic resonator element (11) on the first interior wall of the channel one behind the other in a direction of flow, and further comprising a return flow barrier between the at least two piezoacoustic resonator elements (11), wherein the return flow barrier extends partially across the channel from a second interior wall of the channel opposite the first interior wall, leaving a gap narrower than the channel between the first interior wall of the channel and a distal end of the return flow barrier.

11. The apparatus as claimed in claim 1, comprising at least one additional piezoacoustic resonator element (11), which is arranged so that the excited volume oscillation of the piezoelectric layer (110) of the at least one additional piezoacoustic resonator element (11) is a longitudinal volume oscillation.

12. The apparatus as claimed in claim 1, wherein the piezoacoustic resonator element is arranged on an HF substrate.

13. The apparatus as claimed in claim 1, wherein the volume oscillation of the piezoelectric layer (110) of the piezoacoustic resonator element (11) can be excited with longitudinal mode and with shear mode.

14. The apparatus as claimed in claim 1, wherein the piezoelectric layer (110) is made of one of AlN, PZT and ZnO, having a suitable tilt of the crystallographic c-axis of the hexagonal structure with respect to the layer plane in such a way that a longitudinal volume oscillation and also a shear mode volume oscillation of the piezoelectric layer (110) of the piezoacoustic resonator element (11) can be excited.

15. The apparatus as claimed in claim 1, wherein the piezoacoustic resonator element (11) is made in such a way that by applying a voltage to the piezoelectric layer (110) by means of the electrodes (111, 112) a shear-mode volume oscillation of the piezoelectric layer (110) is excited at resonant frequency, and comprises a surface section arranged for adsorbing the liquid moving through the channel, wherein the resonant frequency of the piezoacoustic resonator element (11) changes depending on the mass of the adsorbed liquid.

16. The apparatus as claimed in claim 15, further comprising two of the piezoacoustic resonator element (11) that are arranged above one another in a stack.

17. The apparatus as claimed in claim 16, wherein a top one of the two resonator elements (11) is a sensor element with a thickness equal to $\lambda/2$.

18. The apparatus as claimed in claim 1, further comprising a further piezoacoustic resonator element which is designed as a sensor element for evaluating the liquid moving through the channel.

19. The apparatus as claimed in claim 1, comprising two of the piezoacoustic resonator element (11) on the first interior wall of the channel between the inlet and the outlet, and further comprising a return flow barrier between the two piezoacoustic resonator elements (11), wherein the return flow barrier extends partially across the channel from a second interior wall of the channel opposite the first interior wall, leaving a gap narrower than the channel between the first interior wall and a distal end of the return flow barrier.

20. The apparatus as claimed in claim 19, further comprising an arm that extends from the distal end of the return flow barrier transverse to an axis of the return flow barrier.

* * * * *